United States Patent [19]

Assal et al.

[11] 4,150,106
[45] Apr. 17, 1979

[54] TOOTHPASTE PERMITTING OF CONTROLLING THE TOOTH BRUSHING TIME

[75] Inventors: Jacques Assal, Lausanne; Bernard Blanc, St. Sulpice; Bernard Monnerat, Fribourg-Moncor, all of Switzerland

[73] Assignee: Cooper S.A., Switzerland

[21] Appl. No.: 895,612

[22] Filed: Apr. 12, 1978

[30] Foreign Application Priority Data

Feb. 16, 1978 [CH] Switzerland .................. 1690/78

[51] Int. Cl.$^2$ .................. A61K 7/16; A61K 7/18; G01N 33/16
[52] U.S. Cl. .................. 424/7; 424/49; 424/52
[58] Field of Search .................. 424/7, 49–58

[56] References Cited

U.S. PATENT DOCUMENTS

| | | | |
|---|---|---|---|
| 1,112,180 | 9/1914 | Westenfelter | 424/7 |
| 1,717,723 | 6/1929 | McCall | 424/7 |
| 2,151,495 | 3/1939 | Bender | 424/7 |
| 3,309,274 | 3/1967 | Brilliant | 424/7 X |
| 3,584,112 | 6/1971 | Morris et al. | 424/7 |
| 3,624,219 | 11/1971 | Perlitsch | 424/7 |
| 3,723,613 | 3/1973 | Block et al. | 424/7 |
| 3,903,252 | 9/1975 | Stearns et al. | 424/7 |
| 3,997,658 | 12/1976 | Block et al. | 424/7 |
| 4,064,229 | 12/1977 | Block et al. | 424/7 |

FOREIGN PATENT DOCUMENTS

| | | | |
|---|---|---|---|
| 106711 | 6/1927 | Austria | 424/7 |
| 2415093 | 10/1974 | Fed. Rep. of Germany | 424/7 |
| 2416272 | 10/1975 | Fed. Rep. of Germany | 424/7 |
| 2203618 | 5/1974 | France | 424/7 |
| 327823 | 7/1935 | Italy | 424/7 |
| 45-35225 | 7/1969 | Japan | 424/7 |
| 74-66839 | 6/1974 | Japan | 424/7 |
| 51-38427 | 9/1974 | Japan | 424/7 |
| 51-38428 | 9/1974 | Japan | 424/7 |
| 51-38429 | 9/1974 | Japan | 424/7 |
| 423858 | 2/1935 | United Kingdom | 424/7 |

*Primary Examiner*—Shep K. Rose
*Attorney, Agent, or Firm*—Robert E. Burns; Emmanuel J. Lobato; Bruce L. Adams

[57] ABSTRACT

This toothpaste contains reagents for controlling the tooth brushing time by the change in color occurring after a predetermined brushing time. It contains essentially a citrate/citric acid buffer having a molarity of 0.07 to 0.35 M and a pH of 4 to 5.5 in the proportion of 10 to 50%, and chlorophenol red in the proportion of 0.02 to 0.1%.

7 Claims, No Drawings

TOOTHPASTE PERMITTING OF CONTROLLING THE TOOTH BRUSHING TIME

FIELD OF THE INVENTION

The present invention relates to a toothpaste containing substances whereby the tooth brushing time can be controlled from the change of color occurring after a predetermined brushing time.

The latest searches in the field of odontology clearly evidenced the preponderant role played by the tooth brushing time, whereas the chemical function of the toothpaste appears to have only a secondary importance. From this it was concluded that the mechanical cleaning of teeth and the massage of gums had a primary importance and should be conducted vigourously, during a minimum time of one to two minutes. Since tooth brushing is regarded as a rather tedious, time-robbing occupation, most people, especially children, hurry over it in most instances while thinking to anything else, so that controlling the duration of the tooth brushing time is rather illusive.

DESCRIPTION OF THE PRIOR ART

Various toothpastes have already been proposed for controlling the brushing time by observing the change of color occurring therein as a consequence of the dilution or pH change taking place due to the incorporation of a suitable reagent therein.

Thus, a known proposition consisted in adding to the toothpaste a substance capable of signalling the acidity of the magma covering the teeth, or an acidity indicator changing to a pH value corresponding substantially to the pH of saliva, but without giving complete and conveniently applicable formulae.

When selecting the component elements, due consideration must be given to the noxiousness, even if it is very low, of the reagents, for it is known that official regulations concerning toxicity are becoming increasingly strict.

SUMMARY OF THE INVENTION

The present invention provides a practical solution to the above-mentioned problem, by proposing the use of only innocuous substances widely accepted in food products. The toothpaste shall be colored by using a pH indicator of which the color appearing in the acid medium at the beginning of the tooth brushing operation changes to a different color when the pH value of the saliva is attained, at the end of the brushing operation.

The toothpaste according to the present invention is characterized in that the reagents incorporated therein comprise essentially a citrate/citric acid buffer having a molarity in the range of 0.07 to 0.35 M and a pH of 4.0 to 5.5, in the proportion of 10% to 50%, and chlorophenol red in the proportion of 0.02 to 0.1%.

The simplest formula consists in taking as base material a conventional toothpaste but free of any alkaline reaction. This toothpaste may contain if desired fluorinated substances and various drugs.

Thus, a citrate/citric acid buffer having a molarity in the range of 0.07 and 0.35 M a pH of 4.0 to 5.5, in the proportion of 10% to 50%, is introduced into this toothpaste, and then chlorophenol red in the proportion of 0.02 to 0.1% is added thereto.

Chlorophenol red is selected because this colored pH indicator is neither toxic nor cancerigenic. It does not stain teeth, stoppings, protheses. Its color in the acid pH range is yellow, and changes to purple in the saliva pH range.

If in the first formula the final pH is set at about 4.5, the buffer capacity (expressed in ml of NaOH 0.1 N/g of toothpaste, utilized in electrometric titration up to pH=7) will normally range between 1.5 and 1.8, and the teeth brushing time, for persons having a saliva pH range of 6 to 7, will be 1 mn 15 sec. to 1 mn 45 sec., according to the pH value and the individual secretion of saliva.

To avoid a certain feeling of acidity which may appear when using the toothpaste according to this first formula, a second formula has been developed which, in addition, is characterized by an improved pH stability.

This second formula comprises:
- a mixture of synthetic polymers (carboxipolymethylenes) and modified celluloses, with a maximum of 3.5%;
- 8 to 25% silicic acid;
- 1 to 6% silica;
- 1.5 to 3% sodium dodecylhydrogensulphate;
- 3 to 4% propandiol;
- 20 to 60% glycerin or sorbitol;
- 0.1 to 0.5% p-hydrobenzoic acid esters;
- 0.02 to 0.1% chlorophenol red;
- 0.01 to 0.04% foodstuff dyes;
- about 1.5% aromas;
- 10 to 50% of a citrate/citric acid buffer having a ionic strength and a pH value calculated to yield a final pH within the range of 4.0 to 5.5 and
- water q.s. 100%.

In order more precisely to define this formula, it may be said that:
- the synthetic polymers (carboxypolymethylene) and the modified celluloses (sodium carragheenate) consist advantageously of a mixture of substantially equal parts of Carbopol 940 and Satiagum B.
- the benzoic acid esters are a mixture of equal parts of methyl p-hydroxybenzoate and propyl p-hydroxybenzoate;
- the citrate/citric acid buffer may advantageously comprise 0.07 M citric acid and 0.07 M sodium citrate set at a pH=4.2 to 4.6;
- the aromas may consist of a mixture of oils of peppermint, anise, cinnamon and augenol or other oils.

Besides, considering that since for commercial reasons the yellow color of the toothpaste is not very attractive, a foodstuff dye such as red or orange for instance corn-poppy red, may be added at a low concentration in order not to interfere with the turning color, while giving a more attractive pink initial color to the product.

Of course, various changes may be brought to this general formula without departing from the basic principle of the invention. Thus, a fluorinated compound and an antiseptic substance may be added to the final product. The following formula constitutes a preferred form of embodiment:

| | |
|---|---|
| - carboxypolymethylene (Carbopol 940) | 1.5% |
| - Sodium carragheenate (Satiagum B) | 1.5% |
| - Silicic acid | 10.0% |
| - Titanium dioxide | 4.0% |
| - Sodium laurylsulphate | 2.1% |
| - 70% Glycerol or Sorbitol | 33.0% |
| - Methyl p-hydroxybenzoate | 0.15% |
| - Propyl p-hydroxybenzoate | 0.15% |
| - Chlorophenol red | 0.05% |
| - Aromas | 1.3% |

| | |
|---|---|
| - Sodium saccharin | 0.5% |
| - Sodium monofluorphosphate | 0.75% |
| - Bromochlorophene | 0.15% |
| - Buffer having a pH value of 4.5 | q.s. 100.0 grams. |

The toothpaste according to this preferred formula has a buffer power within the range of 1.6 to 2.0 and the brushing time necessary before the color turns to purple is 1½ to 2 mn.

Any residual color is removed by simply rinsing with water.

What is claimed is:

1. A toothpaste containing reagents for controlling the tooth brushing time by the change in color occurring after a predetermining brushing time, said reagents comprising essentially a citrate-citric acid buffer having a molarity within the range of 0.07 to 0.35 M with a pH of 4 to 5.5 in the proportion of 10 to 50% and chlorophenol red in the proportion of 0.02 to 0.1%.

2. A toothpaste according to claim 1, having the following composition:
   a mixture, not in excess of 3.5% of synthetic polymers carboxypolymethylenes) and modified celluloses (sodium carragheenate);
   8 to 25% silicic acid;
   1 to 6% silica;
   1.5 to 3% Sodium dodecylhydrogensulphate;
   3 to 4 propandiol;
   20 to 60% sorbitol;
   0.1 to 0.5% p-hydroxybenzoic acid esters;
   0.02 to 0.1% chlorophenol red;
   about 1.5% aromas;
   0.01 to 0.04% foodstuff dyes;
   10 to 50% of a citrate/citric acid buffer having a ionic strength and a pH value adapted to yield a final pH within the range of 4.0 to 5.5;
   water, q.s 100%.

3. Toothpaste according to claim 2, wherein the carboxypolymethylene and carragheenate consist of Carbopol 940 and Satiagum B.

4. A toothpaste according to claim 2, wherein said esters of p-hydroxybenzoic acid are a mixture of methyl p-hydroxybenzoate and popyl p-hydroxybenzoate.

5. A toothpaste according to claim 2, wherein said citrate buffer consists of 0.07 M citric acid and 0.07 M sodium citrate set at a pH of 4.2 to 4.6.

6. Toothpaste according to claim 2, wherein said foodstuff dye is a moderately concentrated corn-poppy red (0.01 to 0.04%) in order not to interfere with the turning of the chlorophenol red to purple red.

7. Toothpaste according to claim 1, of which the preferred composition is:

| | |
|---|---|
| - Carbopol 940 | 1.5% |
| - Satiagum B | 1.5% |
| - Silicic acid | 10.0% |
| - Titanium dioxide | 4.0% |
| - Sodium laurylsulphate | 2.1% |
| - 70% Sorbitol | 33.0% |
| - Methyl p-hydroxybenzoate | 0.15% |
| - Propyl p-hydroxybenzoate | 0.15% |
| - Chlorophenol red | 0.05% |
| - Aromas | 1.3% |
| - Sodium Saccharin | 0.5% |
| - Sodium monofluorophosphate | 0.75% |
| - Bromochlorophene | 0.15% |
| - Buffer : 0.07 M citric acid/ sodium citrate, pH = 4.5 | q.s. 100.00 grams. |

* * * * *